US012011177B2

(12) United States Patent
Fan et al.

(10) Patent No.: US 12,011,177 B2
(45) Date of Patent: Jun. 18, 2024

(54) CLIP PUSHING STRUCTURE FOR CLIP APPLIER

(71) Applicant: MEDSCOPE BIOTECH CO., LTD., Zhunan Township, Miaoli County (TW)

(72) Inventors: Hong-Yang Fan, Zhudong Township (TW); Shih-Hao Huang, Zhudong Township (TW)

(73) Assignee: MEDSCOPE BIOTECH CO., LTD., Zhunan Town (TW)

( * ) Notice: Subject to any disclaimer, the term of this patent is extended or adjusted under 35 U.S.C. 154(b) by 422 days.

(21) Appl. No.: 17/618,773

(22) PCT Filed: Jun. 17, 2020

(86) PCT No.: PCT/CN2020/096573
§ 371 (c)(1),
(2) Date: Dec. 13, 2021

(87) PCT Pub. No.: WO2020/253721
PCT Pub. Date: Dec. 24, 2020

(65) Prior Publication Data

US 2022/0240940 A1 Aug. 4, 2022

(30) Foreign Application Priority Data

Jun. 18, 2019 (CN) ......................... 201910528560.7

(51) Int. Cl.
*A61B 17/128* (2006.01)
*A61B 17/10* (2006.01)

(52) U.S. Cl.
CPC .......... *A61B 17/1285* (2013.01); *A61B 17/10* (2013.01)

(58) Field of Classification Search
CPC .... A61B 17/10; A61B 17/128; A61B 17/1285
See application file for complete search history.

(56) References Cited

U.S. PATENT DOCUMENTS 9,681,877 B2 * 6/2017 Blake, III .......... A61B 17/1285
11,185,329 B2 * 11/2021 Fan ........................ A61B 17/10
(Continued)

FOREIGN PATENT DOCUMENTS

CN 102106746 A 6/2011
CN 206612825 U 11/2017
(Continued)

OTHER PUBLICATIONS

International Search Report for PCT/CN2020/096573 mailed on Aug. 28, 2020.

*Primary Examiner* — Ryan J. Severson
(74) *Attorney, Agent, or Firm* — Birch, Stewart, Kolasch & Birch, LLP

(57) ABSTRACT

A clip pushing structure for a clip applier, which is used to install and push clips. The clip pushing structure comprises: a nail mounting groove piece which has a receiving slot, wherein the clips are placed in the receiving slot of the nail mounting groove piece in a continuous abutting manner; a screw-in ladder member which has a nail-pushing part and a plurality of pushed parts, a pitch being formed between every two pushed parts; a nail pushing member which has a body, a front pushing part that may push the foremost clip, and a rear pushing part that may push each pushed part of the screw-in ladder member; and a clamping jaw which penetrates a clamping jaw assembly, the clamping jaw having two arms which each have a convex part and abut against a left side wall and a right side wall of the clamping jaw assembly.

7 Claims, 10 Drawing Sheets

6

90

(56) References Cited

U.S. PATENT DOCUMENTS

| | | | | |
|---|---|---|---|---|
| 11,918,231 | B2 * | 3/2024 | Whitfield | A61B 17/1222 |
| 2014/0379003 | A1 * | 12/2014 | Blake, III | A61B 17/1285 606/143 |
| 2021/0330329 | A1 * | 10/2021 | Fan | A61B 17/10 |
| 2022/0096091 | A1 * | 3/2022 | Whitfield | A61B 17/083 |
| 2022/0240940 | A1 * | 8/2022 | Fan | A61B 17/1285 |

FOREIGN PATENT DOCUMENTS

| | | | |
|---|---|---|---|
| CN | 108065982 | A | 5/2018 |
| CN | 10979355 | A | 5/2019 |

* cited by examiner

CLIP PUSHING STRUCTURE FOR CLIP APPLIER

BACKGROUND OF THE INVENTION

1. Field of the Invention

The present invention is related to medical equipment, in particular to a clip pushing structure of a clip applier.

2. Description of the Related Art

The known clip pushing structure of the clip applier, which is the structure of the rear spring compressing and pushing the clip, from the beginning to the end. Therefore, when the nails are easily affected by the frictional resistance, the spring force changes and makes the nailing inaccurate. The front push nail is pushed by another element, which is pushed by two different driving elements, so the structure is more complicated, and the accuracy of pushing the nail body forward is poor, and it is easy to cause the front nail body to not be in the correct position and cannot be nailed. Especially when the clip wants to enter the clamping jaw because the clamping jaw will be restrained by the clamping jaw assembly, it lacks flexibility. Therefore, the general practice is to hard squeeze the clip in, and this will cause the clip to fall or the clip cannot enter smoothly, resulting in a situation where the clip is not pushed out. If the clip falls in the human body, it is a very serious problem.

Therefore, the lack of clip pushing structure of the existing clip applier still needs to be improved.

SUMMARY OF THE INVENTION

The present invention has been accomplished under the circumstances in view. It is the main object of the present invention to provide a clip pushing structure of a clip applier, which is simple in structure and easy to operate, and can make the clamping jaw more elastic and can more accurately push the forward position of the nail body.

In order to achieve the above object, the present invention provides a clip pushing structure of a clip applier to install and push clips, in which a nail pitch is formed between every two clips. The clip pushing structure comprises a nail mounting groove piece that has a receiving slot for the placement of the clips in a continuous manner; a screw-in ladder member that comprises a nail-pushing part and a plurality of pushed parts with a pitch defined between each two adjacent pushed parts; a nail pushing member that comprises a body, a front pushing part capable of pushing against the foremost clip and a rear pushing part capable of pushing against each pushed part of the screw-in ladder member; and a clamping jaw passing through a clamping jaw assembly. The clamping jaw comprises two arms. The two arms are respectively provided with a convex part respectively pushed against a left side wall and a right side wall of the clamping jaw assembly. The clamping jaw and the clamping jaw assembly form a clip applying unit.

In this way, while the front pushing part of the nail pushing member pushes the forefront clip, the present invention utilizes the multiple pushed parts of the screw-in ladder member to be driven by the rear pushing part of member, so that the nail-pushing part of the screw-in ladder member more accurately pushes the clip forward, thereby achieving the object of the invention.

Preferably, the nail pitch is equal to the pitch.

Preferably, the clip pushing structure further comprises a lower half tube. The lower half tube comprises a chute. The body of the nail pushing member can be axially movably set on the chute of the lower half tube.

Preferably, the nail mounting groove piece comprises a one-way stop to stop the pushed parts of the screw-in ladder member in one direction, so that the screw-in ladder member can only move forward but not move backward.

Preferably, the nail mounting groove piece comprises a baffle for blocking between one of the pushed parts of the screw-in ladder member and the rear pushing part of the nail pushing member.

The present invention will be described in detail below in conjunction with the drawings and specific embodiments, but not as a limitation of the present invention.

DETAILED DESCRIPTION OF THE INVENTION

Figure 1:
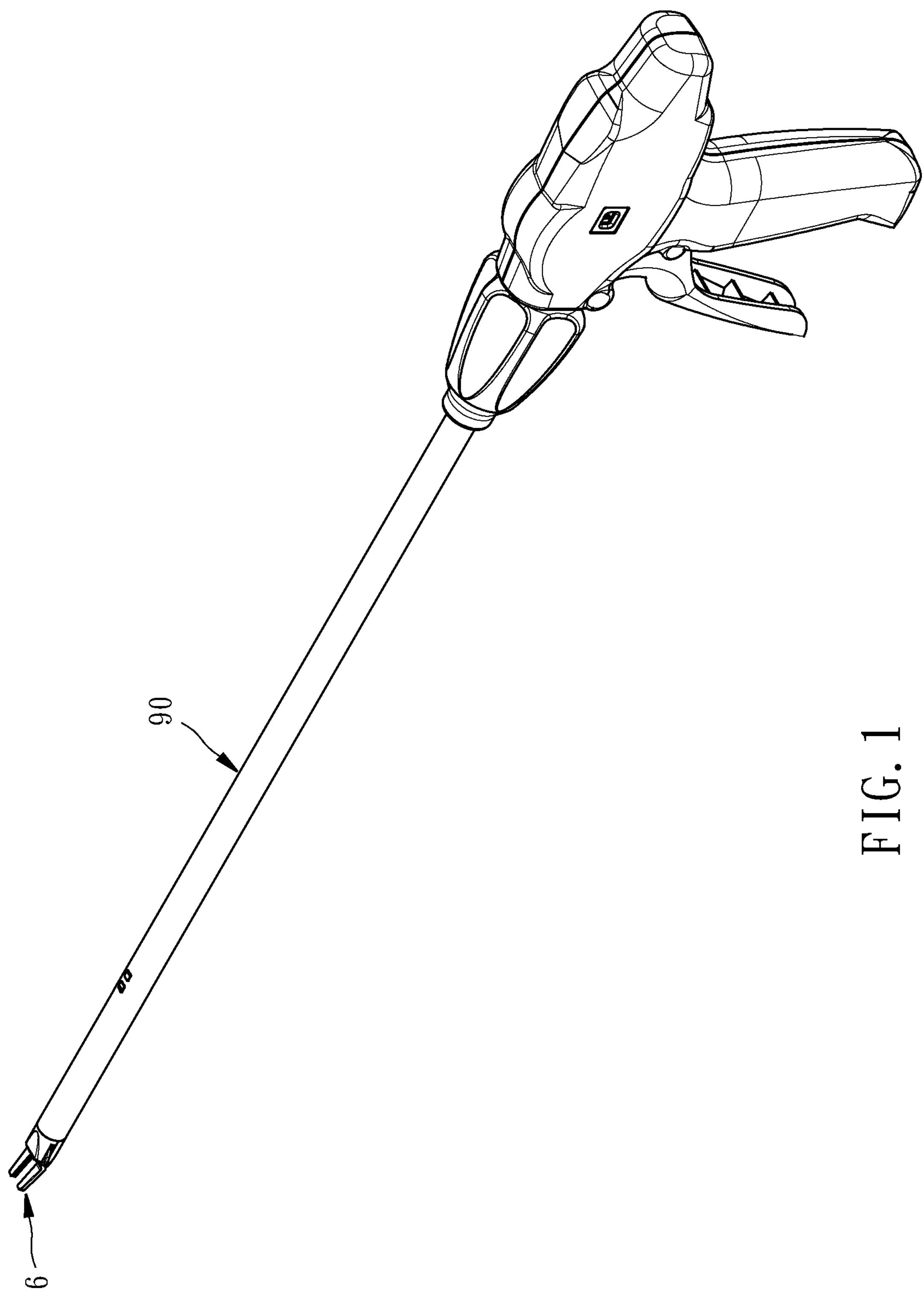
FIG. 1 is an oblique top elevational view of a preferred embodiment of the present invention combined into a clip applier.

The present invention will be further described below in conjunction with the accompanying drawings and the preferred embodiment:

As shown in the drawings, a clip pushing structure of a clip applier provided by the present invention is used to install and push clips (1), wherein a nail pitch (P1) is formed between every two clips (1).

The clip pushing structure of the clip applier comprises a nail mounting groove piece (10), a screw-in ladder member (20), a nail pushing member (30), a lower half tube (40), an upper half tube (50), a clip applying unit (6), and an outer tube (90).

The nail mounting groove piece (10) comprises a receiving slot (12), a one-way stop (13) located in the middle section, and a baffle (14). The one-way stop (13) is used to stop the pushed parts (23) of the screw-in ladder member (20) in one direction for controlling the screw-in ladder member (20) to go forward without going back.

The clips (1) are continuously placed in the receiving slot (12) of the nail mounting groove piece (10).

Figure 4:
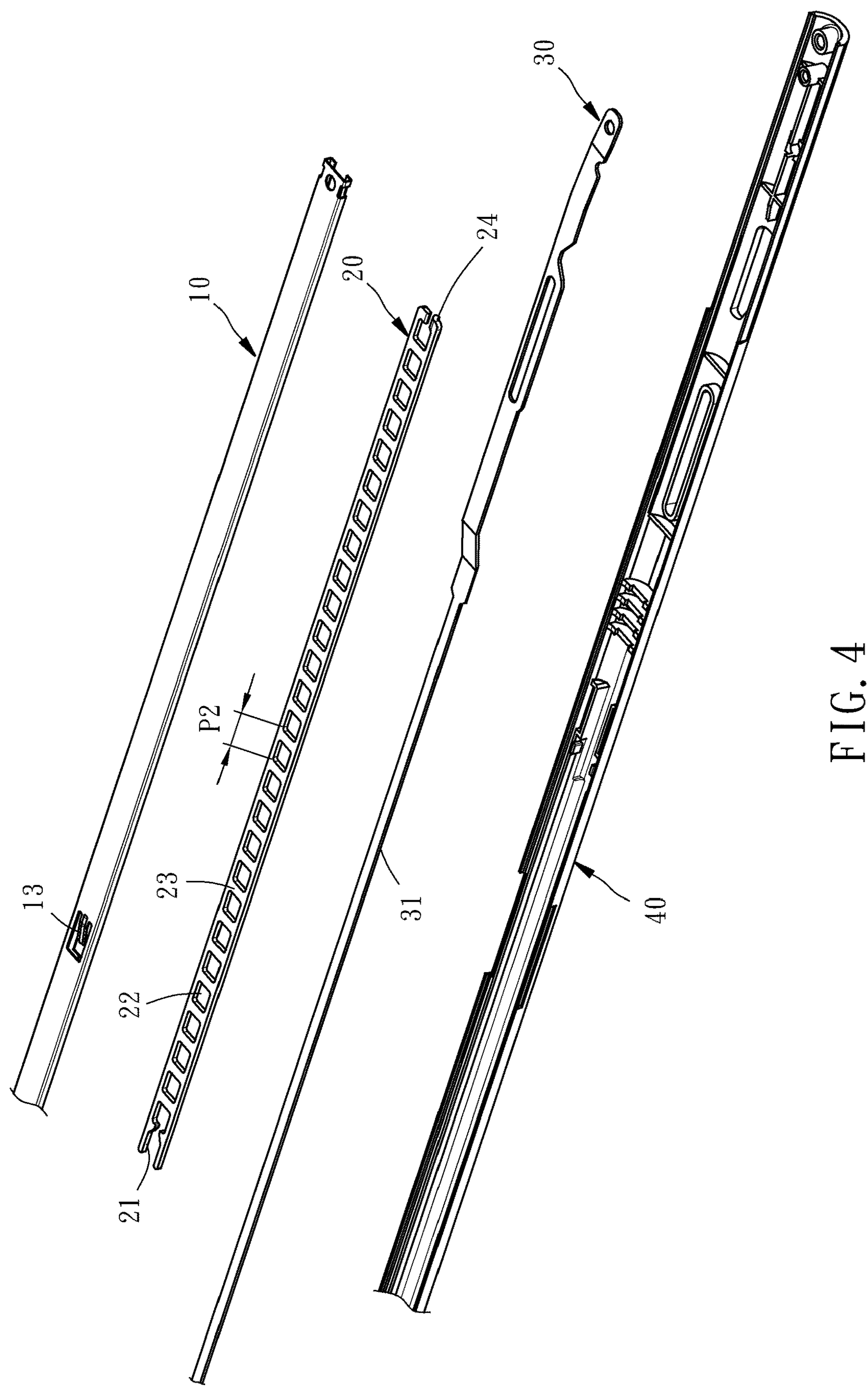
FIG. 4 is another partial exploded view of a preferred embodiment of the present invention.
Figure 9:
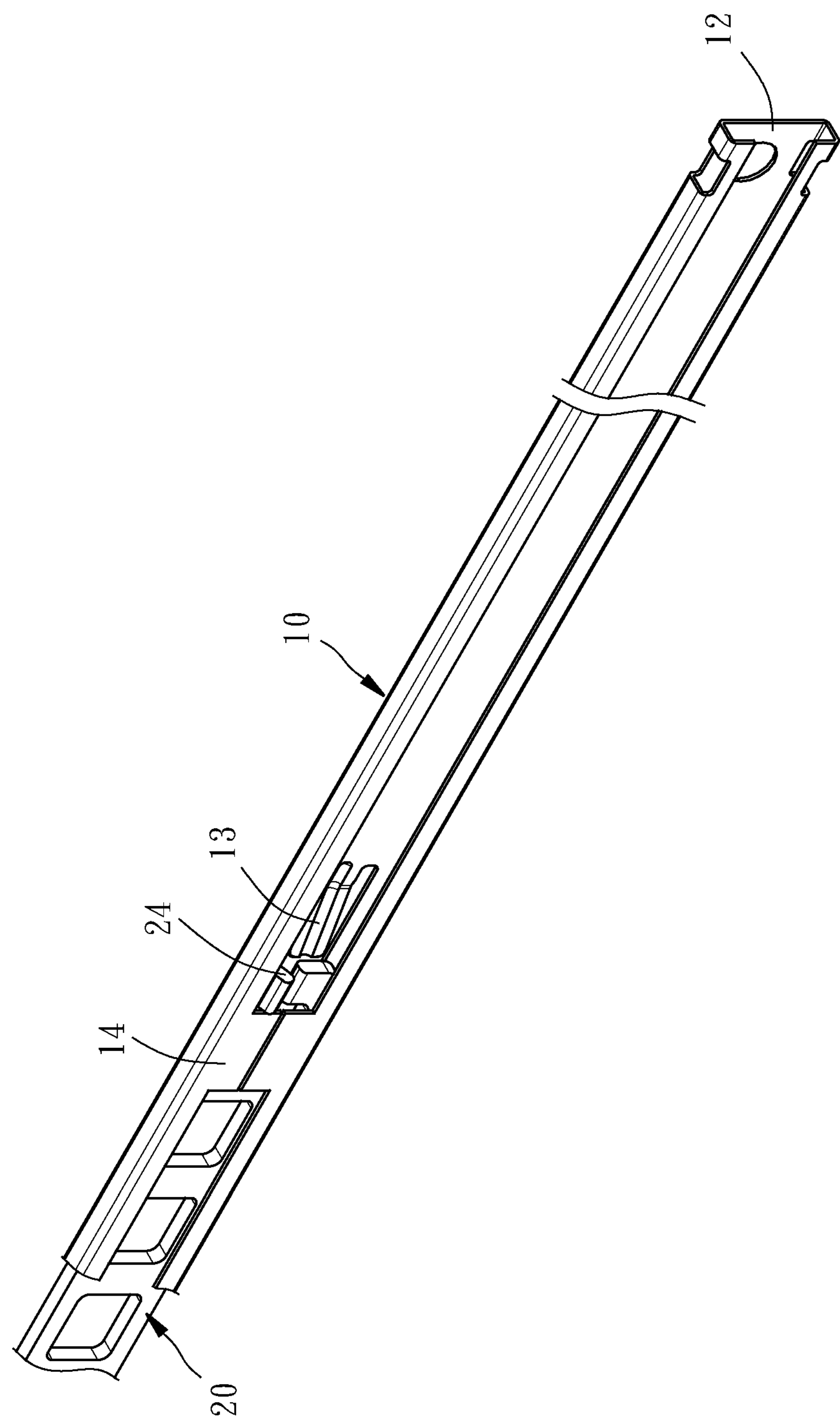
FIG. 9 is a partial view of the combination of the screw-in ladder member and the nail mounting groove piece in a preferred embodiment of the present invention.

The screw-in ladder member (20) comprises a nail-pushing part (21), and a plurality of pushed parts (23). A pitch (P2) is formed between every two pushed parts (23). The screw-in ladder member is provided with a positioning engaging portion (24) protruding outwards at its end, as shown in FIGS. 4 and 9.

The nail pitch (P1) is equal to the pitch (P2).

The one-way stop (13) of the nail mounting groove piece (10) stops the pushed parts (23) of the screw-in ladder member (20) in one direction, so that the screw-in ladder member (20) can only go forward without going back.

The nail pushing member (30) comprises a body (31), a front pushing part (33) that can push against the foremost clip (1), and a rear pushing part (32) that can push against each pushed part (23) of the screw-in ladder member (20).

The baffle (14) of the nail mounting groove piece (10) can be used to block between one of the pushed parts (23) of the screw-in ladder member (20) and the rear pushing part (32) of the nail pushing member (30). The baffle (14) can block at least one pitch (P2) of the rear pushing part (32), so that the screw-in ladder member (20) can only move one pitch (P2) when the nail pushing member (30) moves two pitches (P2).

The lower half tube (40) has a chute (43), and the body (31) of the nail pushing member (30) can be axially movably arranged on the chute (43) of the lower half tube (40).

The upper half tube (50) is combined with the lower half tube (40).

Figure 2:
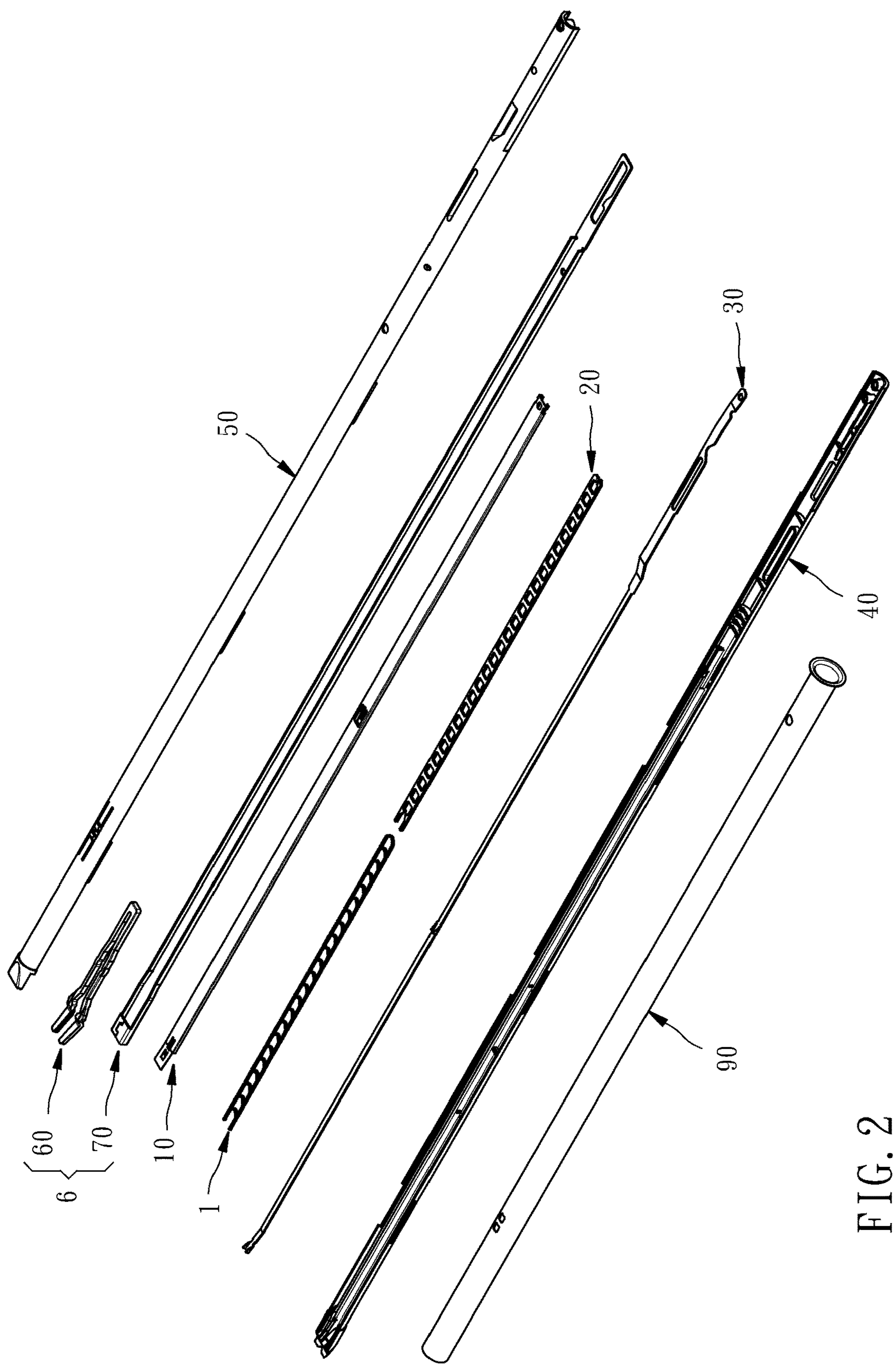
FIG. 2 is an exploded view of a preferred embodiment of the present invention.
Figure 3:
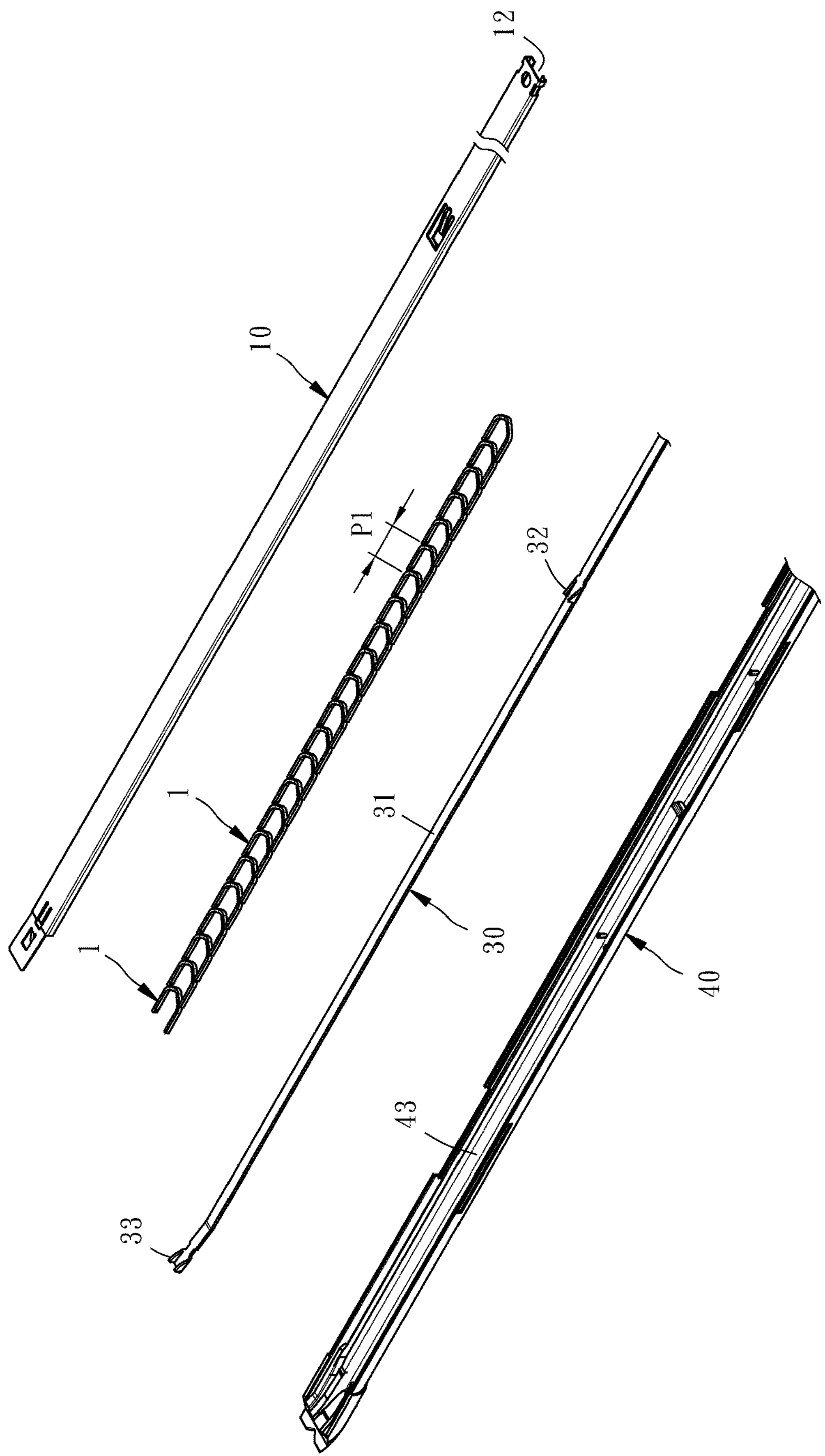
FIG. 3 is a partial exploded view of a preferred embodiment of the present invention.
Figure 5:
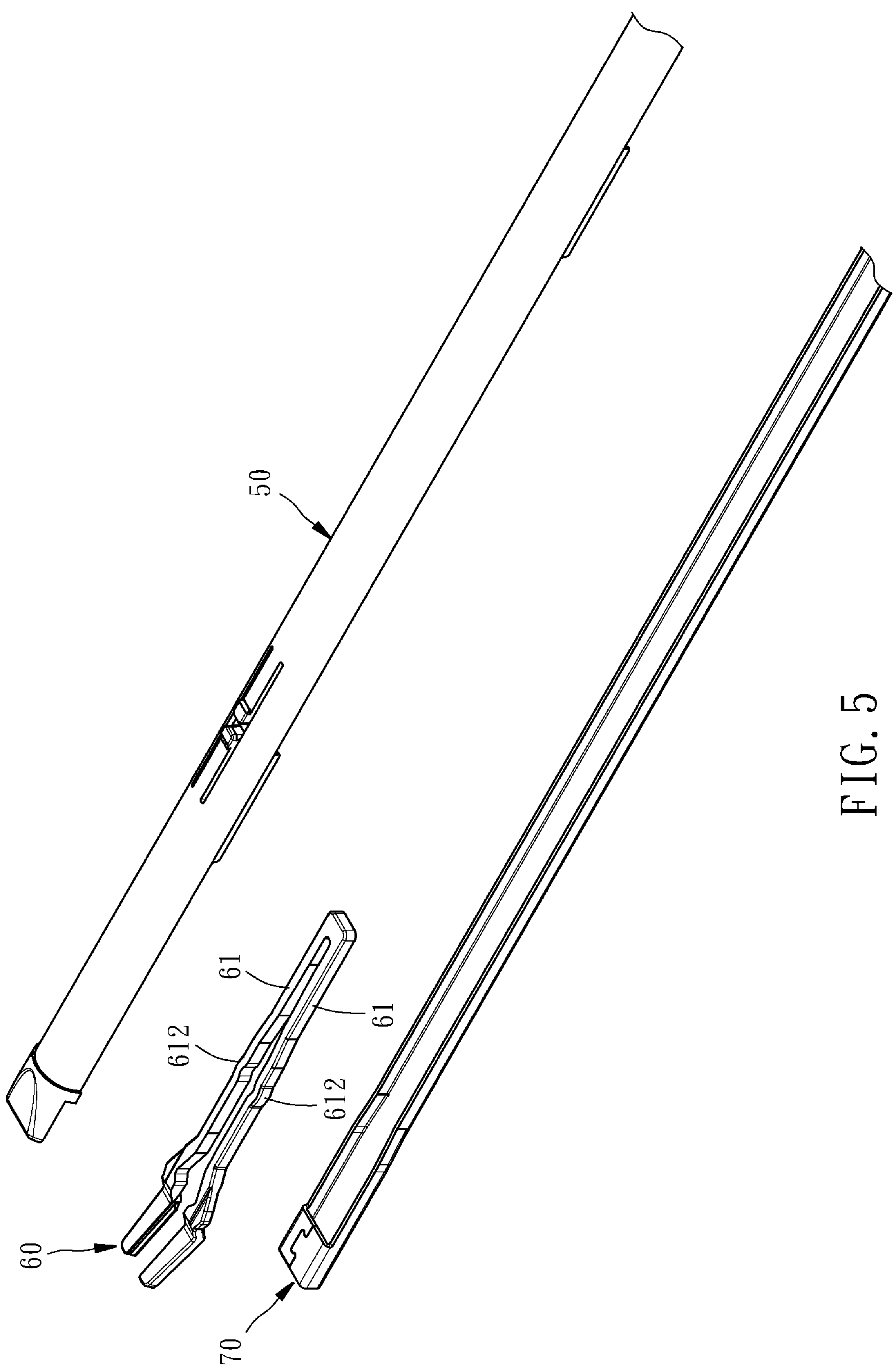
FIG. 5 is still another partial exploded view of a preferred embodiment of the present invention.
Figure 5A:
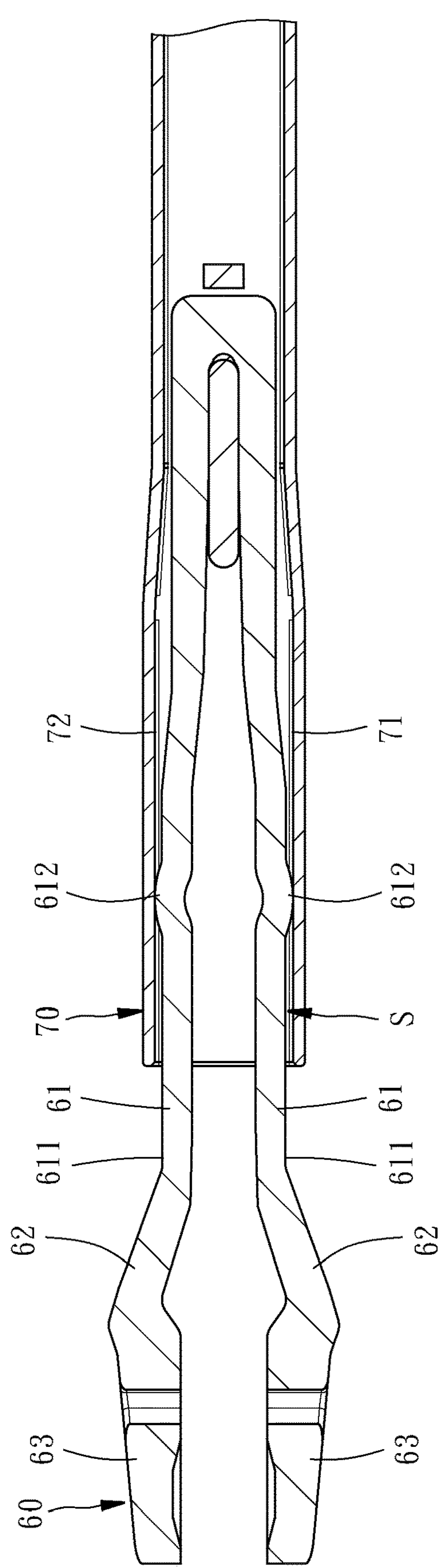
FIG. 5A is a plan view of the clip applying unit of a preferred embodiment of the present invention.

The clip applying unit (6) comprises a clamping jaw (60) and a clamping jaw assembly (70), as shown in FIG. 2, FIG. 5 and FIG. 5A.

The clamping jaw (60) is connected to the upper half tube (50).

The clamping jaw (60) comprises two arms (61). One ends of the two arms (61) are connected to each other, and the other ends of the two arms (61) each extend in the opposite direction to form an outer expansion section (62), and each outer expansion section (62) is extended and connected to a clamping section (63). The clamping jaw (60) is clamped by the two clamping sections (63) close to each other to clamp the clip.

The clamping jaw assembly (70) has a long groove shape with a left side wall (71) and a right side wall (72). The clamping jaw (60) passes through the clamping jaw assembly (70) and is located between the left side wall (71) and the right side wall (72). The two arms (61) of the clamping jaw are provided with a convex part (612) on its outer side (611) close to the corresponding left side wall (71) or right side wall (72), so that the two arms (61) can each use its convex part (612) to abut the wall surface of the corresponding left side wall (71) or right side wall (72). Thereby, the arm outer side (611) between the convex part (612) and the expansion section (62) can form with the left side wall (71) or the right side wall (72) of the clamping jaw assembly a gap S therebetween. Therefore, the two arms (61) can be expanded with a little extra space and flexibility within the range that has not been constrained by the left side wall (71) and the right side wall (72).

In this way, when clip (1) enters the space between the two clamping sections (63), the two clamping sections (63) can be slightly stretched, so that clip (1) can enter the space between the two clamping sections (63) more smoothly to avoid the situation where the clip is dropped or the clip cannot be smoothly entered without being pushed out.

The outer tube (90) is sleeved onto the lower half tube (40) and the upper half tube (50).

With the above structure, when the baffle (14) of the nail mounting groove piece (10) can be used for the nail pushing member (30) to move two nail pitches (P1), the rear pushing part (32) only pushes the screw-in ladder member (20) to move a pitch (P2).

In this way, while the front pushing part (33) of the nail pushing member (30) pushes the forefront clip, the present invention utilizes the multiple pushed parts (23) of the screw-in ladder member (20) to be driven by the rear pushing part (32) of member (30), so that the nail-pushing part (21) of the screw-in ladder member (20) more accurately pushes the clip forward. Because the clamping jaw can be expanded elastically, the clip can enter the space between the clamping sections more smoothly to achieve the purpose of the invention. In addition, when the screw-in ladder member is moved to the end, the positioning engaging portion (24) will cause the screw-in ladder member (20) to be unable to move forward due to the restriction of the baffle (14). In turn, the clip applier can no longer be operated to avoid the situation where the clip applying unit has no nails and empty clips.

Figure 5B:
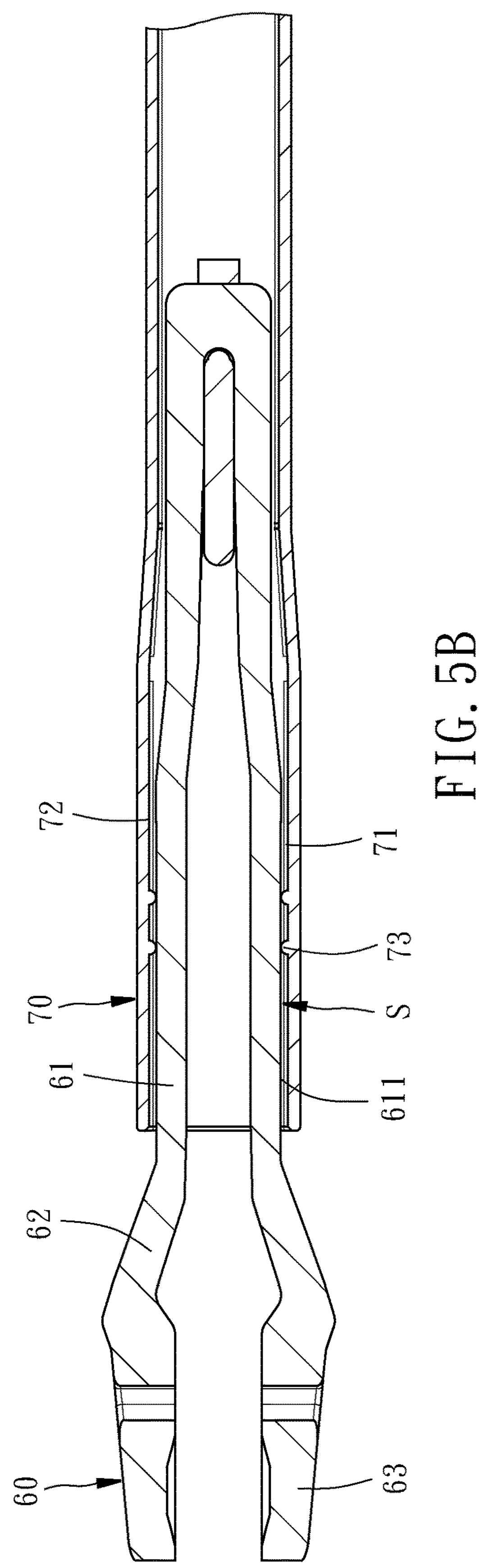
FIG. 5B is a top view of the clip applying unit of another preferred embodiment of the present invention.
Figure 6:
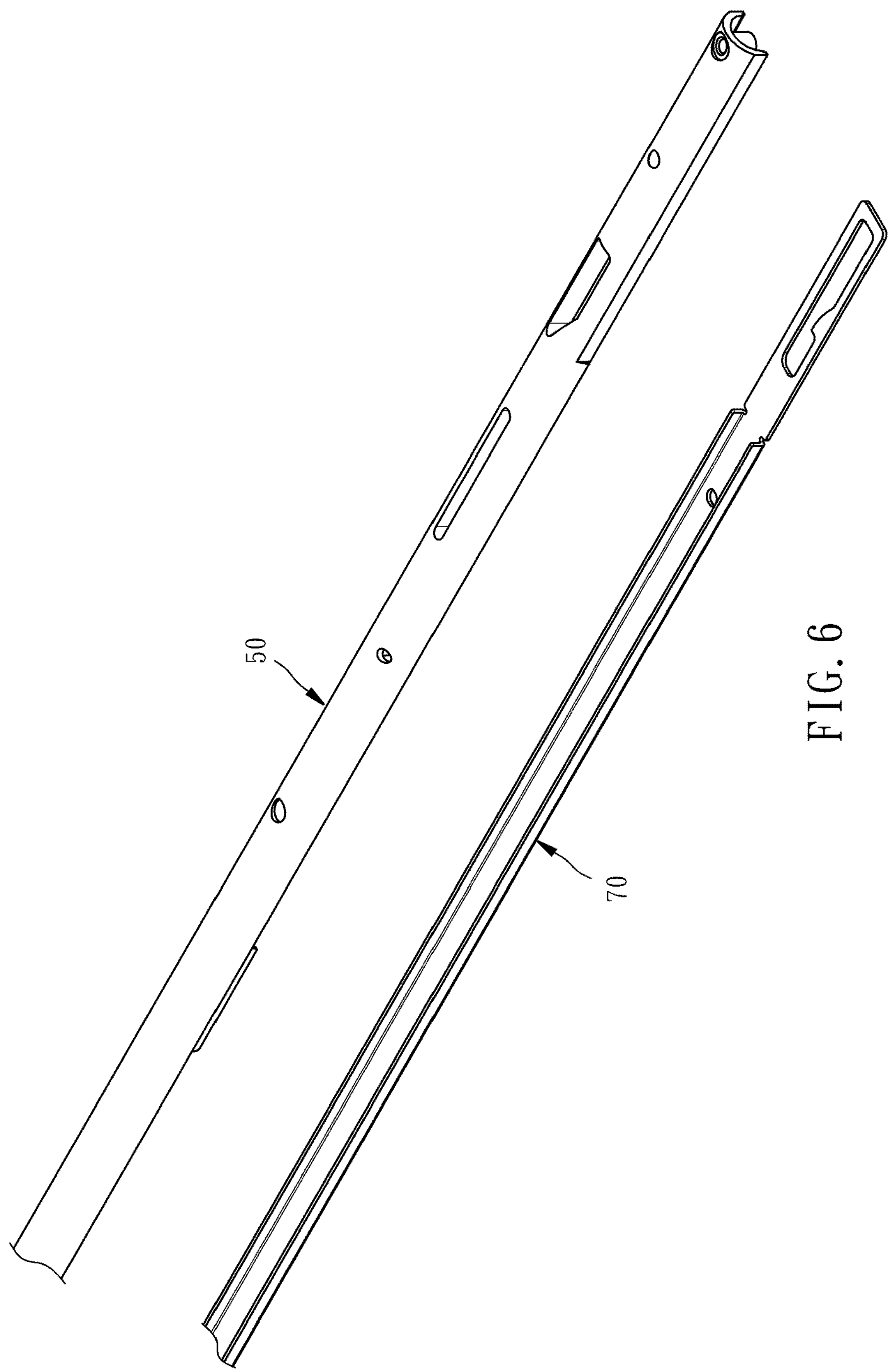
FIG. 6 is another partial exploded view of a preferred embodiment of the present invention.
Figure 7:
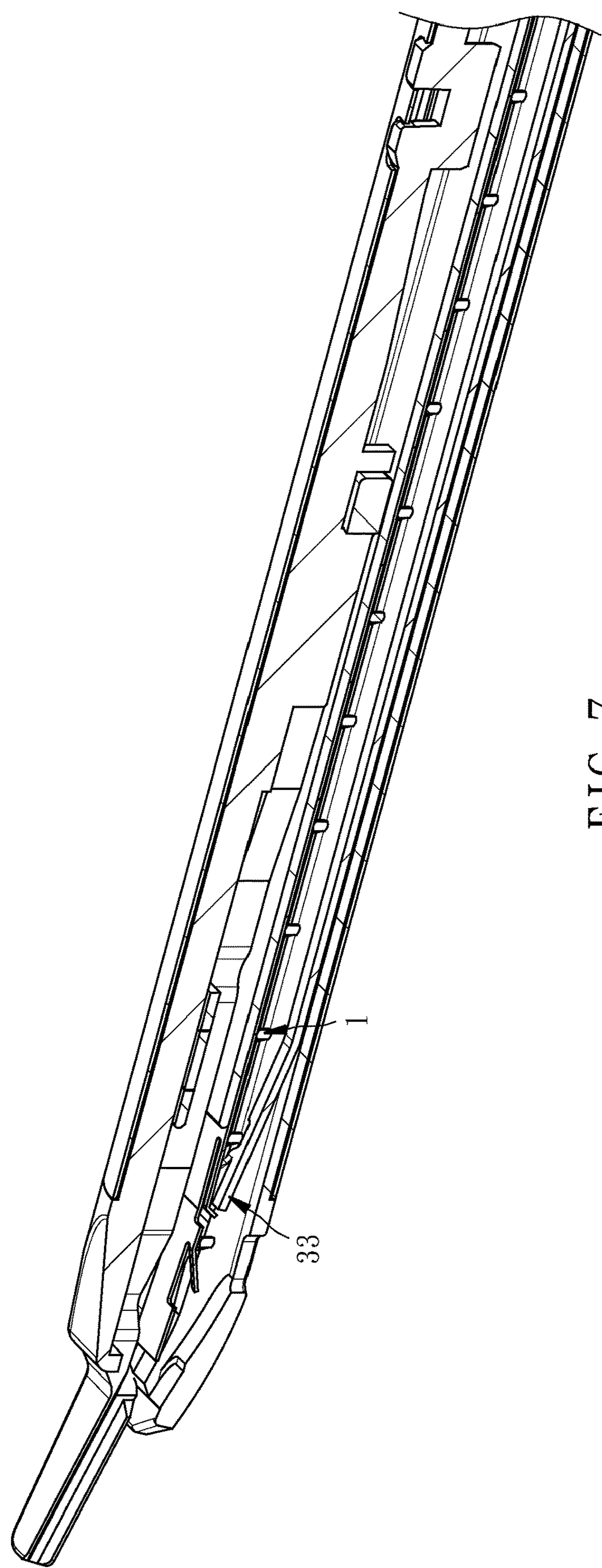
FIG. 7 is a partial view of a combined perspective of a preferred embodiment of the present invention.
Figure 8:
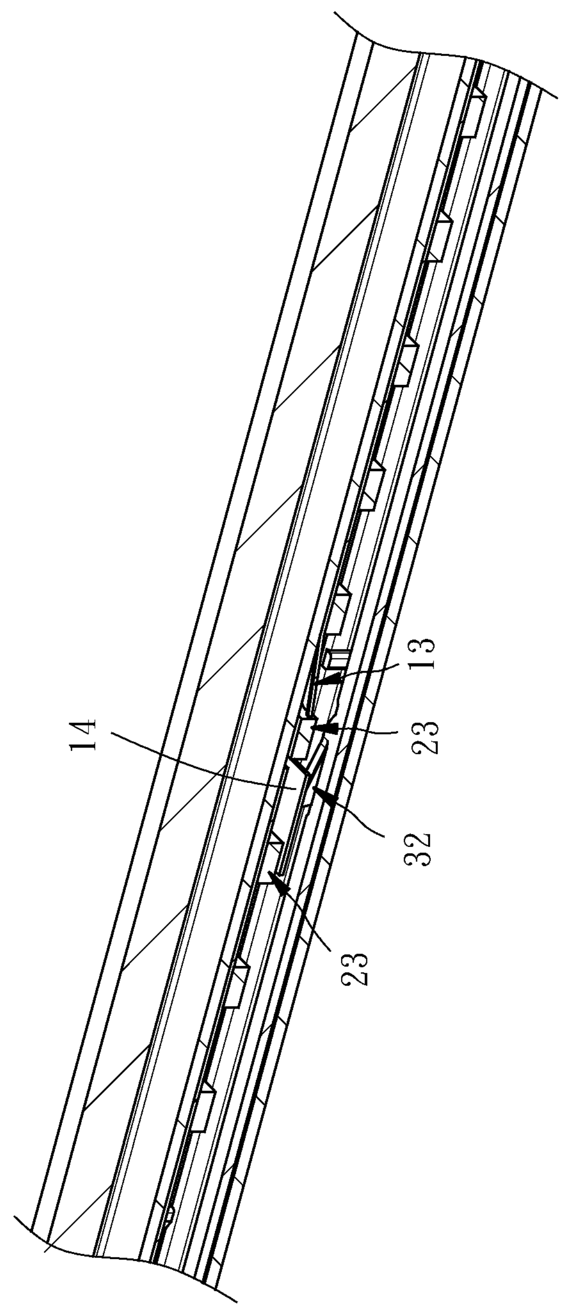
FIG. 8 is a partial view of a combined perspective of a preferred embodiment of the present invention.

Of course, the matching method between the clamping jaw (60) and the clamping jaw assembly (70) is not limited to the convex part (612) being set on each arm (61) of the clamping jaw, and it can also be set in reverse. As shown in FIG. 5B. on the outer side (611) of each arm of the clamping jaw is not provided with a convex part (612). Instead, the left side wall (71) and the right side wall (72) of the clamping jaw assembly are each provided with at least one convex part (73). Similarly, by using the convex parts (73) to press against the outer side walls (611) of the two arms, the arm outer side (611) between the convex part (612) and the expansion section (62) can form with the left side wall (71) or the right side wall (72) of the clamping jaw assembly a gap S therebetween. The gap S can provide a space that can be stretched. Therefore, the two arms (61) can be expanded with a little extra space and flexibility within the range that has not been constrained by the left side wall (71) and the right side wall (72), so that clip (1) can be smoothly pushed into the space between the two clamping sections (63).

Of course, the present invention can also have other various embodiments. Without departing from the spirit and essence of the present invention, those skilled in the art can make various corresponding changes and modifications according to the present invention, but these corresponding changes and modifications all should belong to the protection scope of the claims of the present invention.

What is claimed is:

1. A clip pushing structure of a clip applier, used to install and push clips (1), in which a nail pitch (P1) is formed between every two said clips (1), the clip pushing structure comprising:

- a nail mounting groove piece (10) comprising a receiving slot (12) for the placement of said clips (1) in a continuous manner;
- a screw-in ladder member (20) comprising a nail-pushing part (21) and a plurality of pushed parts (23), each two adjacent said pushed parts (23) defining a pitch (P2) therebetween;
- a nail pushing member (30) comprising a body (31), a front pushing part (33) capable of pushing against the foremost said clip (1), and a rear pushing part (32) capable of pushing against each said pushed part (23) of said screw-in ladder member (20);
- wherein said screw-in ladder member (20) comprises a plurality of openings (22), and said pushed parts (23) are respectively formed between each two adjacent said openings (22), and said nail pushing member (30) pushes against said pushed parts (23) of said screw-in ladder member (20);

wherein said nail pitch (P1) is equal to said pitch (P2);

wherein said nail mounting groove piece (10) comprises a one-way stop (13) used to stop said pushed parts (23) of said screw-in ladder member (20) in one direction for controlling said screw-in ladder member (20) to go forward and prohibiting said screw-in ladder member (20) from going back; and a clip applying unit (6) comprising a clamping jaw (60) and a clamping jaw assembly (70), said clamping jaw (60) comprising two arms (61), said two arms (61) having respective one end thereof connected to each other and respective opposite end thereof extending in the opposite direction and terminating in an expansion section (62) and then a clamping section (63), said clamping jaw assembly (70) having a long groove shape with a left side wall (71) and a right side wall (72), said clamping jaw (60) passing through said clamping jaw assembly (70), wherein a convex part is respectively provided between said two arms and the corresponding said left side wall (71) and said right side wall (72).

2. The clip pushing structure of said clip applier as claimed in claim 1, further comprising a lower half tube (40), said lower half tube (40) comprising a chute (43), wherein said body (31) of said nail pushing member (30) is axially movably set on said chute (43) of said lower half tube (40).

3. The clip pushing structure of said clip applier as claimed in claim 1, wherein said nail mounting groove piece (10) comprises a baffle (14) capable of blocking between at least one said pushed part (23) of said screw-in ladder member (20) and said rear pushing part (32) of said nail pushing member (30).

4. The clip pushing structure of said clip applier as claimed in claim 1, wherein said two arms (61) of said clamping jaw each are provided with one said convex part (612) on an outer side (611) thereof close to the corresponding said left side wall (71) or said right side wall (72).

5. The clip pushing structure of said clip applier as claimed in claim 4, wherein said screw-in ladder member is provided with a positioning engaging portion (24) protruding outwards at a distal end thereof.

6. The clip pushing structure of said clip applier as claimed in claim 1, wherein said left side wall (71) and said right side wall (72) of said clamping jaw assembly and the each have at least one said convex part (73), and said convex parts (73) are used to push against an outer wall (611) of each of said two arms (61).

7. The clip pushing structure of said clip applier as claimed in claim 6, wherein said screw-in ladder member is provided with a positioning engaging portion (24) protruding outwards at a distal end thereof.

* * * * *